US012623037B2

(12) United States Patent
Kersey et al.

(10) Patent No.: US 12,623,037 B2
(45) Date of Patent: May 12, 2026

(54) ELECTRONIC AEROSOL PROVISION SYSTEM AND METHOD

(71) Applicant: NICOVENTURES TRADING LIMITED, London (GB)

(72) Inventors: Robert Kersey, London (GB); Patrick Moloney, London (GB); Darryl Baker, London (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 18/469,658

(22) Filed: Sep. 19, 2023

(65) Prior Publication Data

US 2024/0001056 A1 Jan. 4, 2024

Related U.S. Application Data

(63) Continuation of application No. 15/733,787, filed as application No. PCT/GB2019/051162 on Apr. 26, 2019, now Pat. No. 12,364,825.

(30) Foreign Application Priority Data

Apr. 26, 2019 (GB) ...................................... 1806826

(51) Int. Cl.
*A24F 47/00* (2020.01)
*A24F 40/51* (2020.01)
(Continued)

(52) U.S. Cl.
CPC ............. *A61M 15/06* (2013.01); *A24F 40/51* (2020.01); *A24F 40/53* (2020.01); *A24F 40/60* (2020.01);
(Continued)

(58) Field of Classification Search
CPC ................ A61M 15/06; A61M 11/042; A61M 2016/0015; A61M 2205/3368;
(Continued)

(56) References Cited

U.S. PATENT DOCUMENTS 9,277,770 B2 3/2016 Dooly et al.
2013/0284192 A1* 10/2013 Peleg ...................... A24F 40/53
131/329
(Continued)

FOREIGN PATENT DOCUMENTS

CN 205947116 U 2/2017
EP 3138422 A1 3/2017
(Continued)

OTHER PUBLICATIONS

International Preliminary Report on Patentability for Application No. PCT/GB2019/051162, completed on Jul. 29, 2020, 7 pages.
(Continued)

*Primary Examiner* — Abdullah A Riyami
*Assistant Examiner* — Nelson R. Burgos-Guntin
(74) *Attorney, Agent, or Firm* — BURR & FORMAN LLP

(57) ABSTRACT

An electronic aerosol provision system can include an airflow sensor operable to measure an airflow parameter; a profile recall unit operable to recall one or more inhalation airflow profiles, describing at least one of a velocity or an amount of air inhaled through the electronic aerosol provision system over a course of a puff by a user; and a comparison processing unit operable to compare a measured airflow parameter with at least a first inhalation airflow profile while providing aerosol to the user.

11 Claims, 5 Drawing Sheets

(51) Int. Cl.

| | |
|---|---|
| *A24F 40/53* | (2020.01) |
| *A24F 40/60* | (2020.01) |
| *A24F 40/65* | (2020.01) |
| *A61M 15/06* | (2006.01) |
| *G08B 5/22* | (2006.01) |
| *H04Q 9/00* | (2006.01) |
| *A24F 40/10* | (2020.01) |

(52) U.S. Cl.
CPC ................ *A24F 40/65* (2020.01); *G08B 5/22* (2013.01); *H04Q 9/00* (2013.01); *A24F 40/10* (2020.01)

(58) Field of Classification Search
CPC ........ A61M 2205/50; A61M 2205/502; A61M 2205/8206; A24F 40/51; A24F 40/53; A24F 40/60; A24F 40/65; A24F 40/10; A24F 40/50; A24F 40/485; G08B 5/22; G08B 3/10; H04Q 9/00; A24B 15/167; A24B 15/243
See application file for complete search history.

(56)                  References Cited

U.S. PATENT DOCUMENTS

| | | | |
|---|---|---|---|
| 2013/0340775 A1* | 12/2013 | Juster .................. | H04L 12/1827 |
| | | | 131/273 |
| 2014/0039378 A1 | 2/2014 | Imran | |
| 2014/0261408 A1 | 9/2014 | Wolber et al. | |
| 2014/0270729 A1 | 9/2014 | Depiano et al. | |
| 2015/0020825 A1 | 1/2015 | Galloway et al. | |
| 2015/0216237 A1* | 8/2015 | Wensley ................ | A24F 40/48 |
| | | | 131/273 |
| 2015/0223522 A1 | 8/2015 | Mcclellan et al. | |
| 2015/0230521 A1 | 8/2015 | Talon | |
| 2015/0257445 A1 | 9/2015 | Henry | |
| 2015/0313283 A1 | 11/2015 | Collett et al. | |
| 2015/0320116 A1 | 11/2015 | Bleloch et al. | |
| 2016/0007652 A1 | 1/2016 | Sloan et al. | |
| 2016/0157524 A1* | 6/2016 | Bowen .................. | A24F 40/42 |
| 2016/0331035 A1 | 11/2016 | Cameron | |
| 2016/0338407 A1 | 11/2016 | Kerdemelidis | |
| 2016/0360791 A1* | 12/2016 | Blackley ................ | A24F 40/65 |
| 2016/0361678 A1 | 12/2016 | Blackley | |
| 2016/0366939 A1 | 12/2016 | Alarcon et al. | |
| 2016/0374399 A1 | 12/2016 | Monsees et al. | |
| 2017/0020195 A1 | 1/2017 | Cameron | |
| 2017/0035115 A1 | 2/2017 | Monsees et al. | |
| 2017/0106153 A1 | 4/2017 | Davidson | |
| 2017/0127727 A1 | 5/2017 | Davidson et al. | |
| 2017/0135401 A1 | 5/2017 | Dickens | |
| 2017/0203058 A1 | 7/2017 | Davidson et al. | |
| 2017/0231276 A1 | 8/2017 | Mironov et al. | |
| 2017/0238610 A1 | 8/2017 | Reevell | |
| 2017/0245551 A1 | 8/2017 | Reevell | |
| 2017/0265517 A1 | 9/2017 | Swede et al. | |
| 2017/0266397 A1 | 9/2017 | Mayle et al. | |
| 2017/0280772 A1 | 10/2017 | Batista et al. | |
| 2017/0333645 A1 | 11/2017 | Alizoti et al. | |

FOREIGN PATENT DOCUMENTS

| | | | |
|---|---|---|---|
| JP | 2016525348 A | 8/2016 | |
| JP | 2018504964 A | 2/2018 | |
| RU | 2643603 C2 | 2/2018 | |
| WO | 2013060784 A2 | 5/2013 | |
| WO | 2015063126 A1 | 5/2015 | |
| WO | 2015189556 A1 | 12/2015 | |
| WO | 2016020675 A1 | 2/2016 | |
| WO | 2016091658 A1 | 6/2016 | |
| WO | 2016118645 A1 | 7/2016 | |
| WO | 2018025217 A1 | 2/2018 | |

OTHER PUBLICATIONS

International Search Report and Written Opinion, Application No. PCT/GB2019/051162, mailed Jul. 10, 2019, 16 pages.
Notice of Reasons for Refusal for Japanese Application No. 2020-552320, mailed on Apr. 19, 2022, 8 pages.
Office Action For Russian Application No. 2020134788, mailed on Nov. 25, 2021, 10 pages.
Extended European Search Report issued in corresponding European Application No. 23200376.4 on Jan. 2, 2024, all enclosed pages cited.

* cited by examiner

Air Out
(Into
Mouth)

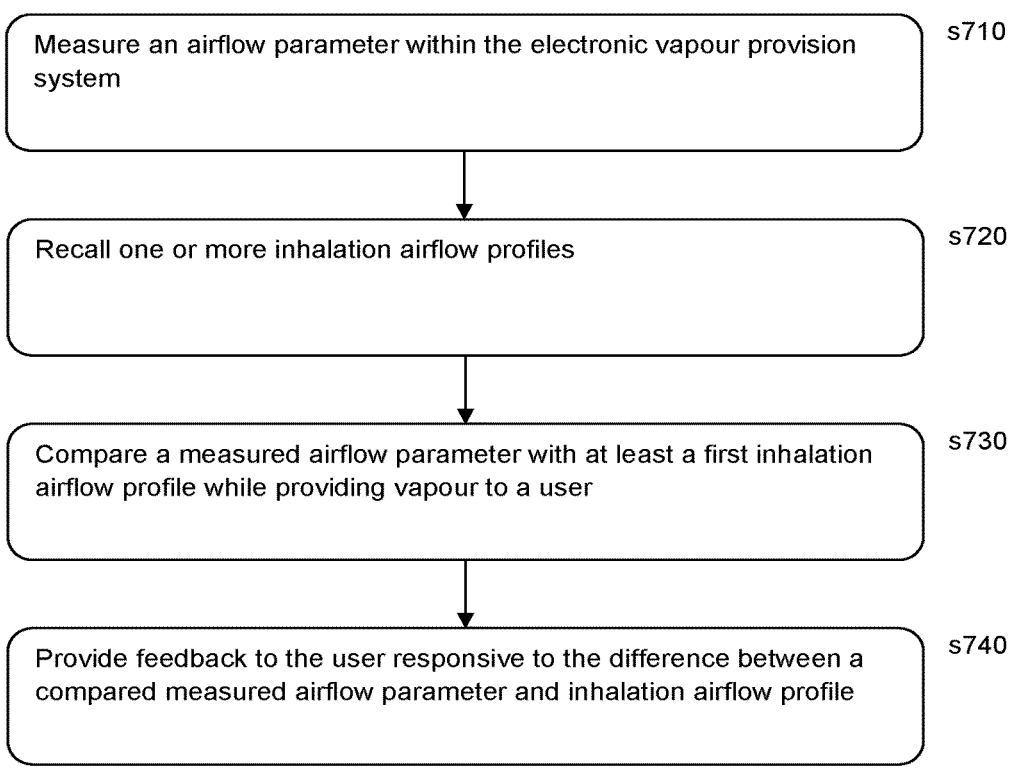

Measure an airflow parameter within the electronic vapour provision system          s710

Recall one or more inhalation airflow profiles          s720

Compare a measured airflow parameter with at least a first inhalation airflow profile while providing vapour to a user          s730

Provide feedback to the user responsive to the difference between a compared measured airflow parameter and inhalation airflow profile          s740

Figure 7

ELECTRONIC AEROSOL PROVISION SYSTEM AND METHOD

PRIORITY CLAIM

The present application is a continuation application of Ser. No. 15/733,787 filed Oct. 26, 2020, which is a National Phase entry of PCT Application No. PCT/GB2019/051162, filed Apr. 26, 2019, which claims priority from GB Patent Application No. 1806826.2, filed Apr. 26, 2018, each of which is hereby fully incorporated herein by reference.

FIELD

The present disclosure relates to electronic aerosol provision systems such as nicotine delivery systems (e.g. electronic cigarettes and the like) and a corresponding method of aerosol provision.

BACKGROUND

Electronic aerosol provision systems such as electronic cigarettes (e-cigarettes) generally contain a reservoir of a source liquid containing a formulation, typically including nicotine, from which an aerosol is generated, e.g. through heat vaporization. An aerosol source for an aerosol provision system may thus comprise a heater having a heating element arranged to receive source liquid from the reservoir, for example through wicking/capillary action. Other source materials may be similarly heated to create an aerosol, such as botanical matter, or a gel comprising an active ingredient and/or flavoring. Hence more generally, the e-cigarette may be thought of as comprising or receiving a payload for heat vaporization.

While a user inhales on the device, electrical power is supplied to the heating element to vaporize the aerosol source (a portion of the payload) in the vicinity of the heating element, to generate an aerosol for inhalation by the user. Such devices are usually provided with one or more air inlet holes located away from a mouthpiece end of the system. When a user sucks on a mouthpiece connected to the mouthpiece end of the system, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

Usually an electric current is supplied to the heater when a user is drawing/puffing on the device. Typically, the electric current is supplied to the heater, e.g. resistance heating element, in response to either the activation of an airflow sensor along the flow path as the user inhales/draw/puffs or in response to the activation of a button by the user. The heat generated by the heating element is used to vaporize a formulation. The released vapor mixes with air drawn through the device by the puffing consumer and forms an aerosol. Alternatively or in addition, the heating element is used to heat but typically not burn a botanical such as tobacco, to release active ingredients thereof as a vapor/aerosol.

The amount of vaporized/aerosolized payload inhaled by the user will depend on how long and how deeply the user inhales, and any heating/vapor flow delay between the beginning of inhalation and disengagement from the device. It is desirable that the user achieves a measure of control over this amount.

SUMMARY

Various approaches are described herein which seek to help address or mitigate this issue.

In a first aspect, an electronic vapor provision system is provided.

In another aspect, a method of electronic vapor provision is provided.

Further respective aspects and features of the disclosure are defined in the appended claims.

BRIEF DESCRIPTION OF THE DRAWINGS

Embodiments of the present disclosure will now be described by way of example with reference to the accompanying drawings, in which:

FIG. 7 is a flow diagram of a method of electronic vapor provision in accordance with an embodiment of the present disclosure.

DETAILED DESCRIPTION

Figure 1:
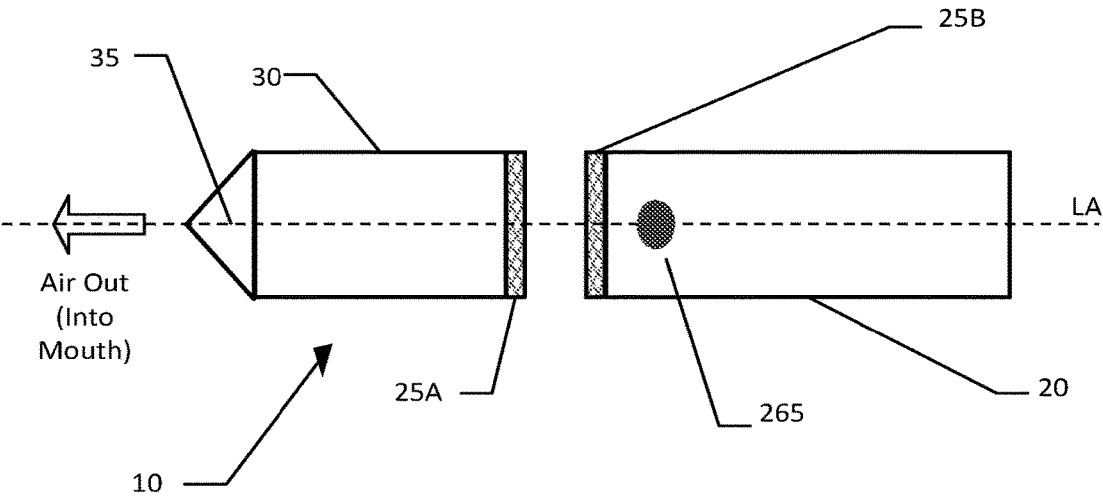
FIG. 1 is a schematic diagram of an electronic vapor provision system in accordance with an embodiment of the present disclosure.

An electronic aerosol provision system and method are disclosed. In the following description, a number of specific details are presented in order to provide a thorough understanding of the embodiments of the present invention. It will be apparent, however, to a person skilled in the art that these specific details need not be employed to practice the present disclosure. Conversely, specific details known to the person skilled in the art are omitted for the purposes of clarity where appropriate.

As described above, the present disclosure relates to an aerosol provision system (e.g. a non-combustible aerosol provision system) or electronic vapor provision system (EVPS), such as an e-cigarette. Throughout the following description the term "e-cigarette" is sometimes used but this term may be used interchangeably with (electronic) aerosol/vapor provision system. Similarly the terms 'vapor' and 'aerosol' are referred to equivalently herein.

Generally, the electronic vapor/aerosol provision system may be an electronic cigarette, also known as a vaping device or electronic nicotine delivery system (END), although it is noted that the presence of nicotine in the aerosolizable material is not a requirement. In some embodiments, a non-combustible aerosol provision system is a tobacco heating system, also known as a heat-not-burn system. In some embodiments, the non-combustible aerosol provision system is a hybrid system to generate aerosol using a combination of aerosolizable materials, one or a plurality of which may be heated. Each of the aerosolizable materials may be, for example, in the form of a solid, liquid or gel and may or may not contain nicotine. In some embodiments, the hybrid system comprises a liquid or gel aerosolizable material and a solid aerosolizable material. The solid aerosolizable material may comprise, for example, tobacco or a non-tobacco product. Meanwhile in some embodiments, the non-combustible aerosol provision system generates a vapor/aerosol from one or more such aerosolizable materials.

Typically, the non-combustible aerosol provision system may comprise a non-combustible aerosol provision device and an article for use with the non-combustible aerosol provision system. However, it is envisaged that articles which themselves comprise a means for powering an aerosol generating component may themselves form the non-combustible aerosol provision system. In one embodiment, the non-combustible aerosol provision device may comprise a power source and a controller. The power source may be an electric power source or an exothermic power source. In one embodiment, the exothermic power source comprises a carbon substrate which may be energized so as to distribute power in the form of heat to an aerosolizable material or heat transfer material in proximity to the exothermic power source. In one embodiment, the power source, such as an exothermic power source, is provided in the article so as to form the non-combustible aerosol provision. In one embodiment, the article for use with the non-combustible aerosol provision device may comprise an aerosolizable material.

In some embodiments, the aerosol generating component is a heater capable of interacting with the aerosolizable material so as to release one or more volatiles from the aerosolizable material to form an aerosol. In one embodiment, the aerosol generating component is capable of generating an aerosol from the aerosolizable material without heating. For example, the aerosol generating component may be capable of generating an aerosol from the aerosolizable material without applying heat thereto, for example via one or more of vibrational, mechanical, pressurization or electrostatic means.

In some embodiments, the aerosolizable material may comprise an active material, an aerosol forming material and optionally one or more functional materials. The active material may comprise nicotine (optionally contained in tobacco or a tobacco derivative) or one or more other non-olfactory physiologically active materials. A non-olfactory physiologically active material is a material which is included in the aerosolizable material in order to achieve a physiological response other than olfactory perception. The aerosol forming material may comprise one or more of glycerine, glycerol, propylene glycol, diethylene glycol, triethylene glycol, tetraethylene glycol, 1,3-butylene glycol, erythritol, meso-Erythritol, ethyl vanillate, ethyl laurate, a diethyl suberate, triethyl citrate, triacetin, a diacetin mixture, benzyl benzoate, benzyl phenyl acetate, tributyrin, lauryl acetate, lauric acid, myristic acid, and propylene carbonate. The one or more functional materials may comprise one or more of flavors, carriers, pH regulators, stabilizers, and/or antioxidants.

In some embodiments, the article for use with the non-combustible aerosol provision device may comprise aerosolizable material or an area for receiving aerosolizable material. In one embodiment, the article for use with the non-combustible aerosol provision device may comprise a mouthpiece. The area for receiving aerosolizable material may be a storage area for storing aerosolizable material. For example, the storage area may be a reservoir. In one embodiment, the area for receiving aerosolizable material may be separate from, or combined with, an aerosol generating area.

FIG. 1 is a schematic diagram of an electronic vapor/aerosol provision system such as an e-cigarette 10 in accordance with some embodiments of the disclosure (not to scale). The e-cigarette has a generally cylindrical shape, extending along a longitudinal axis indicated by dashed line LA, and comprises two main components, namely a body 20 and a cartomizer 30. The cartomizer includes an internal chamber containing a reservoir of a payload such as for example a liquid comprising nicotine, a vaporizer (such as a heater), and a mouthpiece 35. References to 'nicotine' hereafter will be understood to be merely exemplary and can be substituted with any suitable active ingredient. References to 'liquid' as a payload hereafter will be understood to be merely exemplary and can be substituted with any suitable payload such as botanical matter (for example tobacco that is to be heated rather than burned), or a gel comprising an active ingredient and/or flavoring. The reservoir may be a foam matrix or any other structure for retaining the liquid until such time that it is required to be delivered to the vaporizer. In the case of a liquid/flowing payload, the vaporizer is for vaporizing the liquid, and the cartomizer 30 may further include a wick or similar facility to transport a small amount of liquid from the reservoir to a vaporizing location on or adjacent the vaporizer. In the following, a heater is used as a specific example of a vaporizer. However, it will be appreciated that other forms of vaporizer (for example, those which utilize ultrasonic waves) could also be used and it will also be appreciated that the type of vaporizer used may also depend on the type of payload to be vaporized.

The body 20 includes a re-chargeable cell or battery to provide power to the e-cigarette 10 and a circuit board for generally controlling the e-cigarette. When the heater receives power from the battery, as controlled by the circuit board, the heater vaporizes the liquid and this vapor is then inhaled by a user through the mouthpiece 35. In some specific embodiments the body is further provided with a manual activation device 265, e.g. a button, switch, or touch sensor located on the outside of the body.

The body 20 and cartomizer 30 may be detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector 25B on the body 20 that is used to connect to the cartomizer 30 also serves as a socket for connecting a charging device (not shown) when the body 20 is detached from the cartomizer 30. The other end of the charging device may be plugged into a USB socket to re-charge the cell in the body 20 of the e-cigarette 10. In other implementations, a cable may be provided for direct connection between the electrical connector 25B on the body 20 and a USB socket.

The e-cigarette 10 is provided with one or more holes (not shown in FIG. 1) for air inlets. These holes connect to an air passage through the e-cigarette 10 to the mouthpiece 35. When a user inhales through the mouthpiece 35, air is drawn into this air passage through the one or more air inlet holes, which are suitably located on the outside of the e-cigarette. When the heater is activated to vaporize the nicotine from the cartridge, the airflow passes through, and combines with, the generated vapor, and this combination of airflow and generated vapor then passes out of the mouthpiece 35 to be inhaled by a user. Except in single-use devices, the cartomizer 30 may be detached from the body 20 and disposed of when the supply of liquid is exhausted (and replaced with another cartomizer if so desired).

It will be appreciated that the e-cigarette 10 shown in FIG. 1 is presented by way of example, and various other implementations can be adopted. For example, in some embodiments, the cartomizer 30 is provided as two separable components, namely a cartridge comprising the liquid reservoir and mouthpiece (which can be replaced when the liquid from the reservoir is exhausted), and a vaporizer comprising a heater (which is generally retained). As another example, the charging facility may connect to an additional or alternative power source, such as a car cigarette lighter.

Figure 2:
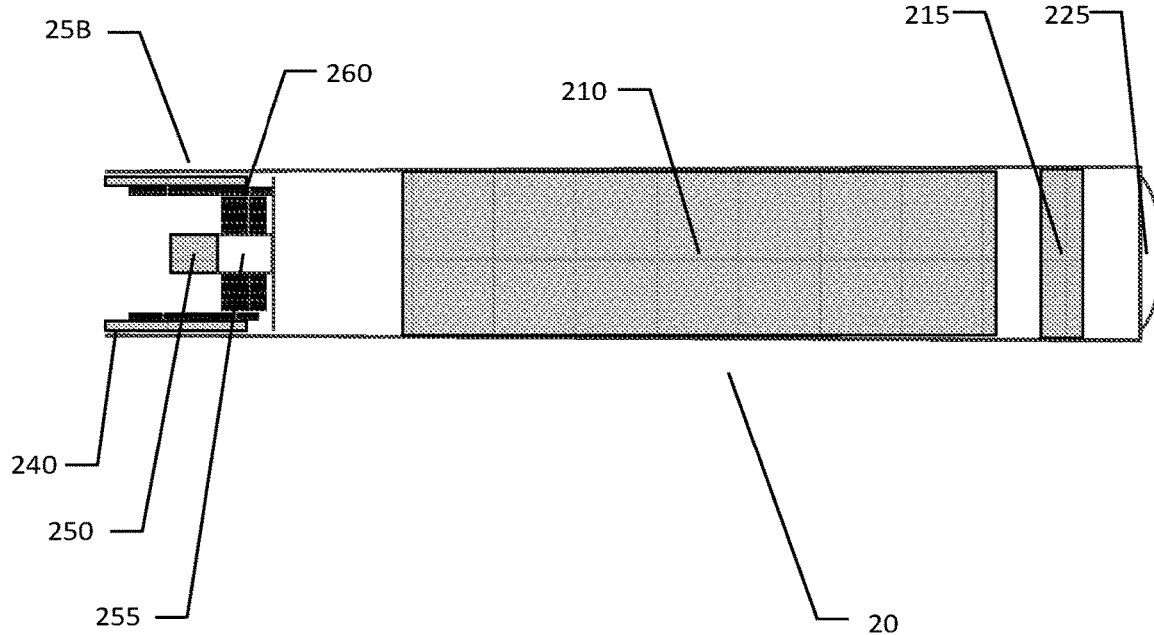
FIG. 2 is a schematic diagram of an electronic vapor provision system in accordance with an embodiment of the present disclosure.

FIG. 2 is a schematic (simplified) diagram of the body 20 of the e-cigarette 10 of FIG. 1 in accordance with some embodiments of the invention. FIG. 2 can generally be regarded as a cross-section in a plane through the longitudinal axis LA of the e-cigarette 10. Note that various components and details of the body, e.g. such as wiring and more complex shaping, have been omitted from FIG. 2 for reasons of clarity.

The body 20 includes a battery or cell 210 for powering the e-cigarette 10 in response to a user activation of the device. Additionally, the body 20 includes a control unit (not shown in FIG. 2), for example a chip such as an application specific integrated circuit (ASIC) or microcontroller, for controlling the e-cigarette 10. The microcontroller or ASIC includes a CPU or micro-processor. The operations of the CPU and other electronic components are generally controlled at least in part by software programs running on the CPU (or other component). Such software programs may be stored in non-volatile memory, such as ROM, which can be integrated into the microcontroller itself, or provided as a separate component. The CPU may access the ROM to load and execute individual software programs as and when required. The microcontroller also contains appropriate communications interfaces (and control software) for communicating as appropriate with other devices in the body 10.

The body 20 further includes a cap 225 to seal and protect the far (distal) end of the e-cigarette 10. Typically there is an air inlet hole provided in or adjacent to the cap 225 to allow air to enter the body 20 when a user inhales on the mouthpiece 35. The control unit or ASIC may be positioned alongside or at one end of the battery 210. In some embodiments, the ASIC is attached to a sensor unit 215 to detect an inhalation on mouthpiece 35 (or alternatively the sensor unit 215 may be provided on the ASIC itself). An air path is provided from the air inlet through the e-cigarette, past the airflow sensor 215 and the heater (in the vaporizer or cartomizer 30), to the mouthpiece 35. Thus when a user inhales on the mouthpiece of the e-cigarette, the CPU detects such inhalation based on information from the airflow sensor 215.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A of the cartomizer 30, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

As mentioned above, a button 265, which represents a form of manual activation device 265, may be located on the outer housing of the body 20. The button 265 may be implemented using any appropriate mechanism which is operable to be manually activated by the user—for example, as a mechanical button or switch, a capacitive or resistive touch sensor, and so on. It will also be appreciated that the manual activation device 265 may be located on the outer housing of the cartomizer 30, rather than the outer housing of the body 20, in which case, the manual activation device 265 may be attached to the ASIC via the connections 25A, 25B. The button 265 might also be located at the end of the body 20, in place of (or in addition to) cap 225.

Figure 3:
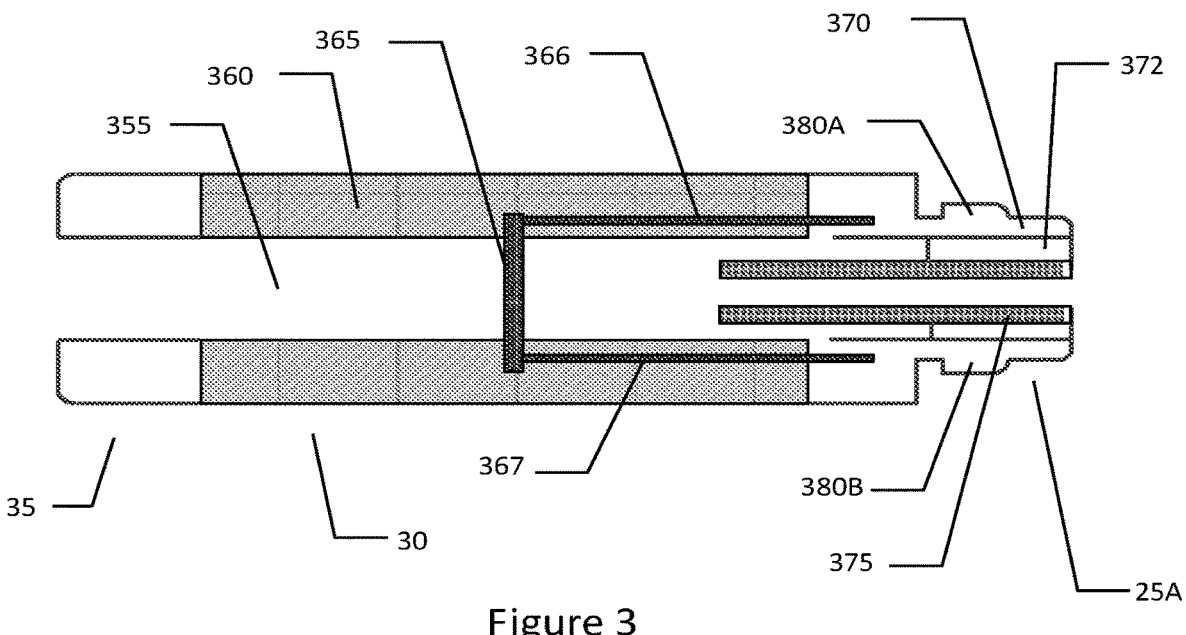
FIG. 3 is a schematic diagram of an electronic vapor provision system in accordance with an embodiment of the present disclosure.

FIG. 3 is a schematic diagram of the cartomizer 30 of the e-cigarette 10 of FIG. 1 in accordance with some embodiments of the disclosure. FIG. 3 can generally be regarded as a cross-section in a plane through the longitudinal axis LA of the e-cigarette 10. Note that various components and details of the cartomizer 30, such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer 30 to the body 20. A reservoir of liquid 360 is provided around the air passage 335. This reservoir 360 may be implemented, for example, by providing cotton or foam soaked in liquid. The cartomizer 30 also includes a heater 365 for heating liquid from reservoir 360 to generate vapor to flow through air passage 355 and out through mouthpiece 35 in response to a user inhaling on the e-cigarette 10. The heater 365 is powered through lines 366 and 367, which are in turn connected to opposing polarities (positive and negative, or vice versa) of the battery 210 of the main body 20 via connector 25A (the details of the wiring between the power lines 366 and 367 and connector 25A are omitted from FIG. 3).

The connector 25A includes an inner electrode 375, which may be silver-plated or made of some other suitable metal or conducting material. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heater 365 in the cartomizer 30 via supply lines 366 and 367 as appropriate.

The cartomizer connector 370 is provided with two lugs or tabs 380A, 380B, which extend in opposite directions away from the longitudinal axis of the e-cigarette 10. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer and body are held in a fixed position relative to one another, with minimal wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
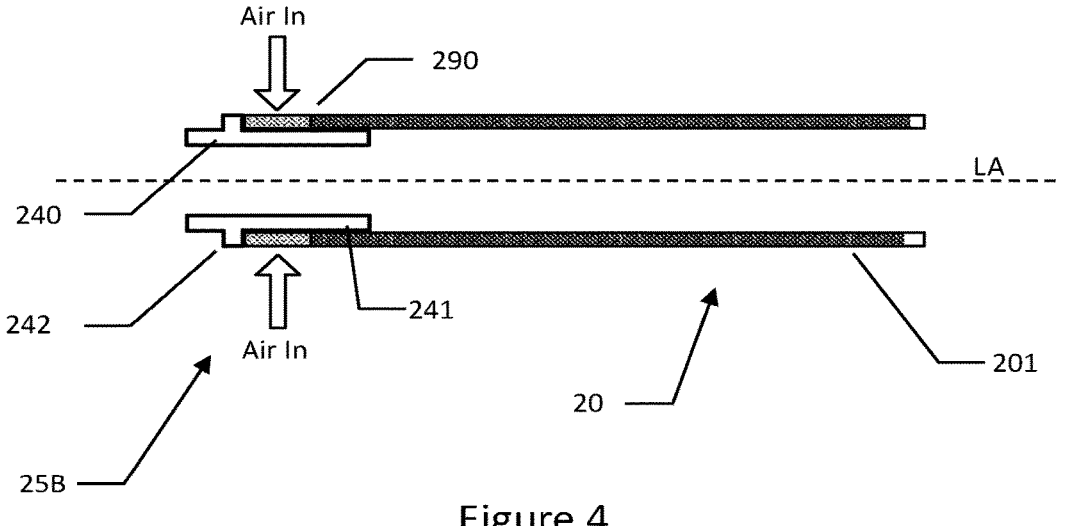
FIG. 4 is a schematic diagram of an electronic vapor provision system in accordance with an embodiment of the present disclosure.

FIG. 4 is a schematic diagram of certain details of the connector 25B at the end of the body 20 in accordance with some embodiments of the disclosure (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar. The external housing 201 may also comprise the manual activation device 265 (not shown in FIG. 4) so that the manual activation device 265 is easily accessible to the user.

The body connector 240 extends from this external housing 201 of the body 20. The body connector 240 as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion does not overlap with the external housing 201, is a collar or sleeve 290, which is again in a shape of a cylindrical tube. The collar 290 is retained between the lip portion 242 of the body connector 240 and the external housing 201 of the body, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow when a user inhales on the mouthpiece 35. However, in some embodiments the majority of air that enters the device when a user inhales flows through collar 290 and body connector 240 as indicated by the two arrows in FIG. 4.

Figure 5:
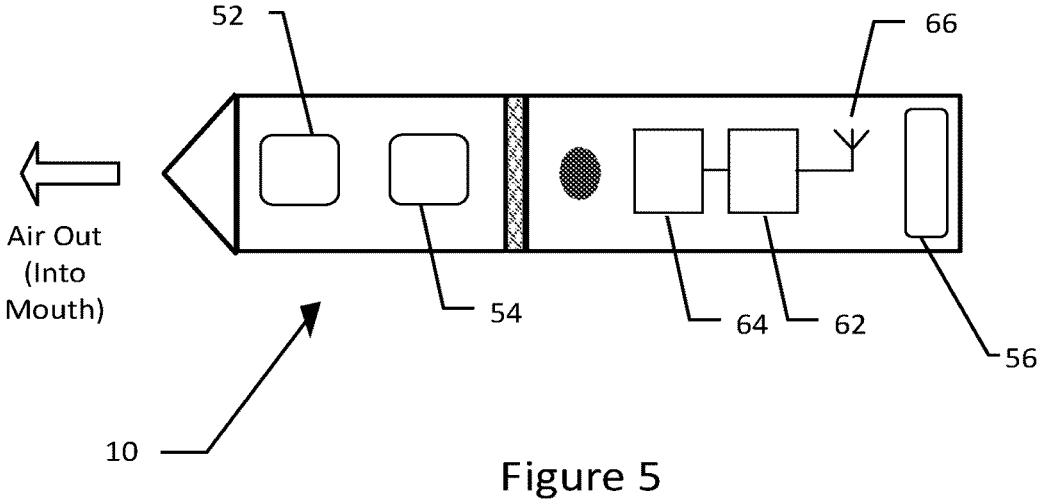
FIG. 5 is a schematic diagram of an electronic vapor provision system in accordance with an embodiment of the present disclosure.

Referring now also to FIG. 5, in an embodiment of the present disclosure, an electronic vapor provision system (EVPS) 10 such as one of those described previously herein is adapted to provide its user with feedback. The feedback is provided in relation to one or more predefined inhalation airflow profiles. An inhalation airflow profile describes the velocity and/or amount of air inhaled through the electronic cigarette of the EVPS over the course of a puff by the user.

Such profiles may thus characterize a short, low-dosage puff, or a long, higher dosage puff. Similarly the profiles may vary depending on whether the user's inhalation is shallow or deep. Hence the profile may be of arbitrary length, depending on the corresponding inhalation behavior, and the airflow parameter described by the profile may vary over that time as the characteristics of the user's inhalation varies.

Optionally a profile may be predefined at manufacture or by a distributor, or may be loaded later by a user.

A profile is typically defined parametrically, to optionally varying degrees of approximation. A profile may thus define a target shape of an inhalation as a time history or curve, or may define the peak airflow (or a similar measure of intensity) and the duration for the inhalation profile, or may define the integral of the airflow and the time, in either case optionally together with one or more further parameters responsive to the inhalation curve (such as a timing for a peak within the inhalation).

The inhalation performed by a user may thus be compared to the profile description, whether this is by tracing inhalation with respect to a time history or curve, or comparing the difference between a target profile position on an inhalation intensity/time plot and the user's current position, either after an inhalation is complete, or as it progresses.

In addition, optionally a profile may be taught by the user in a training mode, where the user performs the desired inhalation and this is measured (as will be discussed later herein). Optionally an average of a plurality of such inhalations may be used to create an inhalation profile.

Optionally, with a suitable interface (such as one provided by a mobile phone) a profile may be defined through a user interface, or an existing profile may be edited to create a custom profile without training by use of one or more example inhalation.

Profiles may then subsequently be selected by the user, and/or selected by the EVPS according to one or more criteria such as: the time of day (for example having a short and/or shallow puff during working hours, and a longer and/or deeper puff in the evenings); day of week (for example having a short and/or shallow puff during weekdays, and a longer and/or deeper puff on the weekends; the user's location (if at least one component of the EVPS can use a GPS signal, or associate a location with a BlueTooth® or WiFi ID); type of vapor being provided (for example as a function of nicotine concentration, flavor or the like); the present power of the EVPS; and similarity to the measured airflow parameter (in other words, selecting the closest profile to the actual inhalation). In the case of the type of vapor, a profile may be associated with a particular payload. The may be accessed (for example downloaded) by use of a QR code or other identifier on the payload's packaging, or by use of a code that can be parsed to reconstruct the profile (for example, the possible permutations of just four letters allow for identifying nearly half a million different profiles).

Profiles may be absolute values, such that only one is selected (e.g. only based on time of day, but not day of week)

and/or may be relative or cumulative with respect to a selected profile or a baseline or neutral profile, so that for example on a weekend evening, both the time of day and day of week profiles combine to further lengthen/deepen the inhalation profile (for example) compared to a week day or office hours alone. The current payload strength and/or the current power setting of the EVPS may then further modify such a profile, and so on.

Hence profiles may be predefined, added during use, or may be defined or trained by the user, and may subsequently be chosen individually, or if formatted appropriately, may optionally be combined.

As noted above, the user might train the EVPS with a particular profile. In order to perform such inhalation training, and also in order to compare a user's inhalation with an existing profile, the EVPS is operable to generate a measured airflow parameter that varies over time in response to airflow.

Accordingly, according to aspects of the present disclosure, the EVPS comprises an airflow measurement unit or means (for example airflow sensor 215) within the e-cigarette that is operable to generate a measured airflow parameter that varies over time in response to airflow.

The airflow measurement means may detect airflow speed, and optionally in conjunction with the cross sectional area of the channel in which it performs the measurement, estimate the current volume of air being inhaled (for instance for successive measurement periods or sample periods of the measurement means). Alternatively or in addition, any suitable air speed or volume flow sensor (collectively referred to as an air flow measurement means) may be used. Hence one or more air flow measurement means of one or more types may be used as appropriate.

This airflow parameter may then be used to train a profile, or subsequently to compare current usage with an existing profile, as noted above.

To store and/or access one or more profiles (whether predefined by manufacturer, user-defined or trained), in embodiments of the present invention the EVPS comprises a profile recall unit or means operable to recall one or more inhalation airflow profiles.

The profile recall means may comprise local data storage, such as a RAM or flash memory 64. Alternatively or in addition, the recall means may comprise communication means (66) operable to communicate with a remote server, to obtain one or more inhalation airflow profiles associated with an account of the user. This option will be described in more detail later herein.

In order to compare a current inhalation action by the user with one or more profiles, a comparison processing unit or means 62 (such as the aforementioned control unit or ASIC) is operable to compare a measured airflow parameter with at least a first inhalation airflow profile, while providing vapor to a user.

In other words, during normal use of the EVPS when delivering vapor to a user, the measured airflow parameter is compared with the profile (for example at regular sample intervals in the order of tenths, hundredths or thousandths of seconds, depending on the desired precision of the system) to calculate any difference.

In this way, the user's deviation from the intended inhalation profile can be calculated as a function of time. Optionally, a cumulative deviation or difference can be calculated from this difference data. As noted above, this deviation may be with respect to an inhalation curve or time history for a profile puff, or may be with respect to a parametric summary of the puff, such as a target intensity and duration.

A feedback unit or means is then operable to provide feedback to the user responsive to the difference between a measured airflow parameter and inhalation airflow profile (that is, a comparison is made between the measured airflow parameter and an inhalation airflow profile).

Advantageously, this allows the user to become aware of when their inhalation action differs from that of the current profile. This enables a user to correct or adapt their inhalation action over time, training themselves to inhale in a preferred manner.

The feedback can be real-time (i.e. during inhalation) and/or provided after inhalation is complete.

The feedback can take one or more forms, as described below.

In one instance, the feedback may comprise a haptic feedback (52) in which a haptic output is proportional to the difference between the compared measured airflow parameter and inhalation airflow profile.

Hence for example the EVPS may comprise a buzzer (52) or similar vibration generator whose amplitude and/or frequency can be adjusted proportional to the difference between the compared measured airflow parameter and inhalation airflow profile. The user can then feel the vibration through their fingers as the hold the device and/or through their lips.

The feedback can be real-time (i.e. during inhalation) so that the haptic output is an instantaneous reflection of how the user is deviating from the profile, enabling them to correct their inhalation action and attempt to track the profile by minimizing the haptic feedback that they feel. Alternatively or in addition, haptic feedback may be provided after inhalation is complete, for example as a vibration for a predetermined period whose amplitude or frequency is proportional to the total difference between the user's inhalation and the profile.

Figure 8:
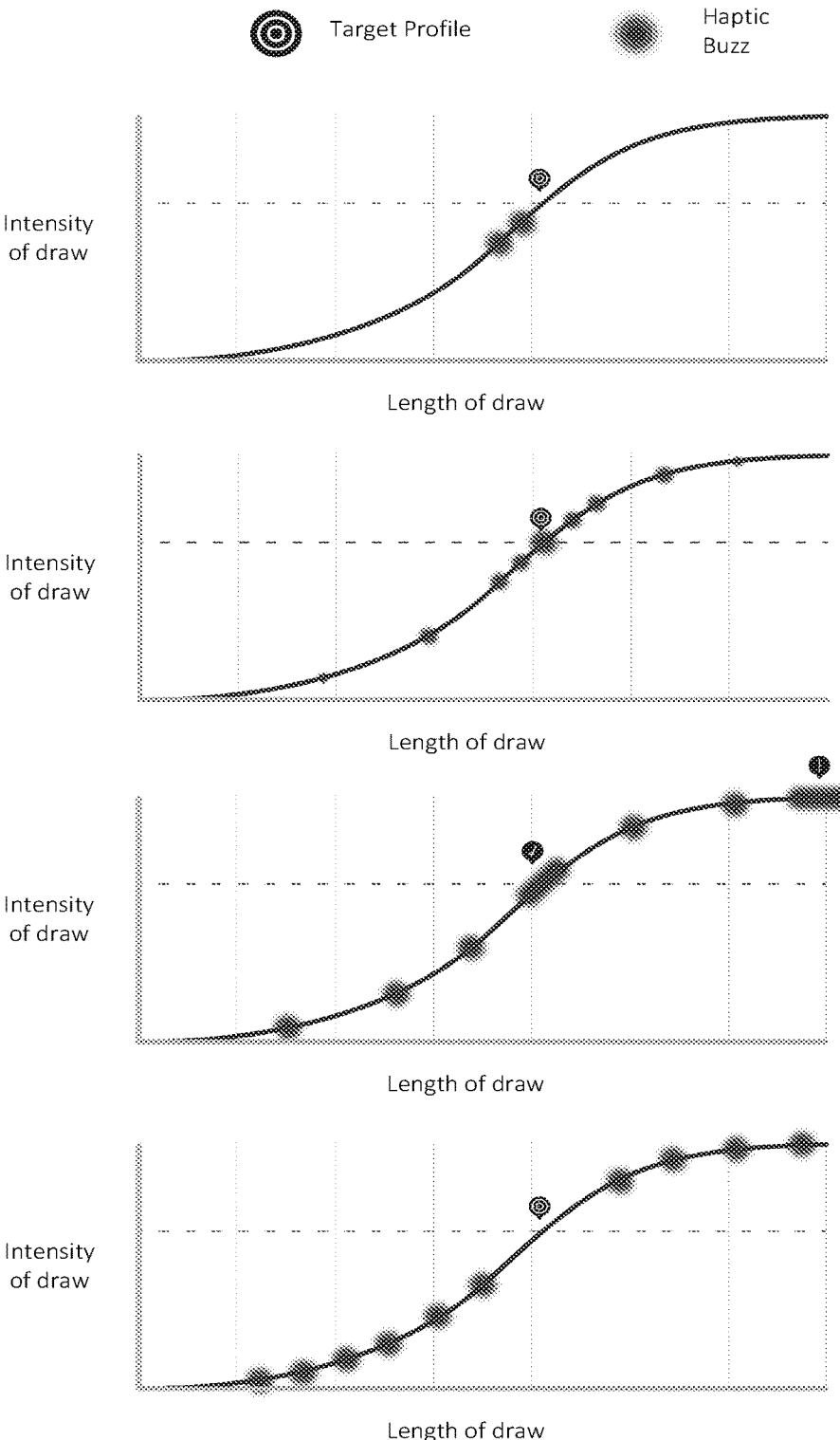
FIG. 8 is a schematic diagram illustrating example haptic feedback for an electronic vapor provision system in accordance with an embodiment of the present disclosure.

FIG. 8 provides several examples of haptic feedback for an example profile. The profile, shown in FIG. 8, is a 'performance' profile, either pre-set at manufacture, downloaded, or trained by the user, which is intended to provide a desired amount of active ingredient to the user.

FIG. 8 illustrates four exemplary haptic feedback modes for a target profile, here defined as a preferred combined intensity and duration. In the first example, a double haptic buzz is provided just prior to or at the point where the user approaches the target profile position. In the second example, the strengths of the haptic buzzes are proportional to how close the user is to the target profile position. In the third example, the duration of haptic buzzes are either proportional to how close the user is to the target, or change to a longer duration within a predetermined threshold distance of the target profile position. This third example also illustrates the option of a haptic warning if the user exceeds the range of one or more preferred usage parameters (here, intensity and/or duration). Meanwhile in the fourth example, a low-level haptic feedback ceases when the user is close to the target profile position.

It will be appreciated that the above haptic grammars are exemplary, and that others may similarly be used to convey such information.

It will similarly be appreciated that the above profile is exemplary, and that others may be used. For example, a second profile may be a 'minimal' profile, intended to reduce the amount of vapor exhaled by the user as a cloud. The user may then receive feedback that guides the user to this lower intensity, shorter duration inhalation target.

Alternatively or in addition, the feedback may comprise an audio feedback (54) in which an audio output is proportional to the difference between the compared measured airflow parameter and inhalation airflow profile, or provides an audio analogue of one of the haptic examples of FIG. 8, with haptic intensity represented by volume and/or pitch.

Hence for example the EVPS may comprise a loudspeaker, audio-frequency vibration device or other sound generator (54), and as with haptic feedback, the amplitude and/or frequency may vary either instantaneously during inhalation and/or to modify a predetermined output presented after inhalation is complete.

Alternatively or in addition, the feedback may comprise a visual feedback (56) in which a visual output is proportional to the difference between the compared measured airflow parameter and inhalation airflow profile, or provides a visual analogue of one of the haptic examples of FIG. 8, with haptic intensity represented by brightness, color and/or the area illuminated.

Hence for example the EVPS may comprise a light (56) that may change brightness and/or color, and again the brightness and/or color may vary either instantaneously during inhalation and/or to modify a predetermined output presented after inhalation is complete. Hence for example the light might be red for 'warning', and the light gets brighter as the difference increases. Alternatively, the light might be green for 'success', and the light gets brighter as the difference decreases. Alternatively the light may change color according to a so-called 'traffic light' scheme, so that on the basis of one or more threshold difference values, the light may be green when the difference is small, yellow when the difference is medium and red when the difference is large (with small, medium and large being either a design choice or empirically derived).

Alternatively or in addition to a light, the EVPS may comprise a display (not shown in FIG. 5). The display may provide a graphical representation of the profile and also the user's inhalation, based on the measured airflow parameter or a suitably processed value based upon it. The user's inhalation may be shown as a function of time (if the user can see the display during inhalation) or may be shown after inhalation is complete. The display may, for example, be located on a body on the EVPS, for example on the side (which may provide more space for information, but may be harder to see in use) or on or parallel to a top surface comprising the mouthpiece (which may be more readily visible during inhalation, but may provide comparatively less information.

Optionally other information such as whether the difference between the profile and the current inhalation was better than a difference for a previous inhalation (or rolling average of differences) may also provide the user with a sense of progress and motivation to continue self-training.

Similarly optionally, advice based on an interpretation of the difference data may be provided, such as a message reading 'inhale more/less at the beginning/middle/end' (as appropriate) or similar.

As noted above, the feedback is typically responsive to a real-time comparison between the compared measured airflow parameter and inhalation airflow profile, for example based on difference calculations at the measurement sampling rate or an integer number thereof.

The effective frequency of comparison may vary depending on the feedback mechanism(s) chosen. Hence for example, if a display allocated 256 pixels to a profile chart, and the average inhalation by a user lasts 1 second, then a comparison roughly every $\frac{1}{250}^{th}$ of a second may be appropriate even if the airflow parameter is measured ever $\frac{1}{1000}^{th}$ of a second. In such a case, optionally either every $4^{th}$ sample may be used, or samples may be accumulated or averaged between comparisons.

Similarly, if a buzzer only vibrates between 20 and 100 Hz, then an update rate of more than 100 Hz may not be needed.

Also as noted above, the feedback may alternatively or in addition be presented to the user after inhalation is complete, for the most recent puff or for a puff history.

Hence for example such feedback may comprise a haptic feedback in which a one of a plurality of predetermined haptic outputs is selected in response to the difference between the compared measured airflow parameter and inhalation airflow profile. Such a predetermined response may relate to an overall difference between the user's inhalation and a profile (e.g. relating to a small, medium or large error thresholds, based on design choice or empirical selection), or may relate to common patterns of difference, such as too much or too little inhalation at the start or end of the puff which could be respectively represented by four different feedback signals or patterns). Hence the system can use a feedback grammar to summarize how the user deviated from a particular profile.

This approach may also be used for the audio and light-based feedback mechanisms described previously, and also may be used to drive a more complex display, for example by selecting pre-determined text messages. Clearly more complex feedback may also be possible, such as showing the difference between the user's inhalation airflow and the effective target values in the profile.

Like the real-time feedback, an advantage of the feedback provided is that it allows the user to understand how their inhalation deviates from that of the profile, so that they can attempt to more closely match the profile in future.

The profiles can be selected, downloaded, edited or trained by the user so that they reflect the user's desired usage of the device (or example at certain times and/or for certain payloads, and/or at certain locations as determined for example by GPS or BlueTooth® or WiFi IDs (for example at work, at home or in the car).

It should be appreciated that feedback may be provided relative to one or more profiles. For example, in the case of a digital display, the user may be presented with feedback relative to two or more profiles. That is, the user may see that their inhalation closely correlates to a first profile (e.g., a shallow puff) but does not correlate particularly strongly to a second profile (e.g., a deep puff). This could be used when a user wishes to train themselves away from a first puff profile and towards a different puff profile. Alternatively, the device may provide feedback related to the puff profile that is closest to that particular puff. For example, the user may routinely inhale using both a shallow puff and a deep puff. In this implementation, the device is configured to provide feedback relative to which of the two profiles (which may be pre-selected by the user or based on historical usage data for the user) is closer to the user's real-time inhalation, which may vary between a shallow puff or a deep puff, for example. This can mean that the user is provided with an indication as to how far their puff action is away from pre-determined or pre-selected profiles.

Referring again to FIG. 5, the EVPS may be a self-contained unit (commonly referred to as an e-cigarette, even if the device itself does not necessarily conform to the shape or dimensions of a conventional cigarette). Such an e-cigarette may comprise the airflow measuring means, the profile recall means, the comparison processing means and one or more feedback means such as haptic, audio and/or light/display means.

Figure 6:
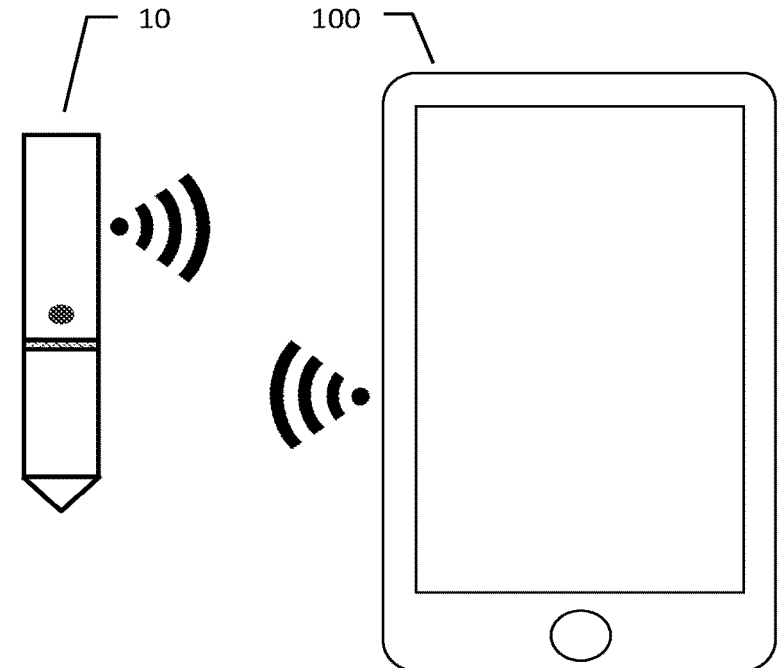
FIG. 6 is a schematic diagram of an electronic vapor provision system in accordance with an embodiment of the present disclosure.

Alternatively, referring to FIG. 6, the EVPS may comprise two components, such as an e-cigarette 10 and a mobile phone or similar device (such as a tablet) 100 operable to communicate with the e-cigarette (for example to at least receive data from the e-cigarette), for example via Bluetooth®.

The mobile phone may then comprise one or more of the profile recall means, the comparison processing means, and one or more feedback means such as haptic, audio and/or light/display means.

A non-limiting and non-exhaustive set of example configurations include:

Firstly, an EVPS comprising an e-cigarette 10 operable to communicate with a mobile phone 100, in which the mobile phone stores one or more profiles and receives airflow measurement data from the e-cigarette, performs the comparison and displays a visual representation of the difference between the user's inhalation and the profile.

Secondly, the EVPS of the first example, in which the mobile phone instructs the e-cigarette to output feedback via one or more means (e.g. vibration, audio and/or light).

Thirdly, the EVPS of the first or second example, in which the mobile phone wirelessly accesses one or more profiles associated with an account of the user at a remote server.

Fourthly, an EVPS comprising an e-cigarette 10 operable to communicate with a currently paired mobile phone 100, in which the e-cigarette stores one or more profiles and the currently paired mobile phone receives at least a first profile and airflow measurement data from the e-cigarette, performs the comparison and displays a visual representation of the difference between the user's inhalation and the profile.

It will be appreciated that the third and fourth examples illustrate arrangements where the access to the profile data is not reliant on a particular mobile phone, either because it is stored in the e-cigarette, or because it is stored remotely. This allows a user to still benefit from the techniques described herein even if they switch, for example, from a work phone to a home phone during the day.

It will also be appreciated that the system may work asynchronously; hence for example the e-cigarette may record airflow parameters for some or all puffs in a period when it is not in communication with a phone, and then subsequently transfer that data to a mobile phone that can present the feedback to the user. Similarly, a user interface on the mobile phone might be used for recalling or setting a profile for use, and this is transmitted to the e-cigarette, which may then perform the comparison and provide feedback based on this profile even if not currently in communication with the mobile phone.

Other combinations of functionality and output will be apparent to the skilled person.

With regards to recalling profiles from a remote server, such a server may hold one or more profiles in association with a respective user account. An app launched on the mobile phone of the EVPS (when comprising a mobile phone) then transmits to the server relevant user account access data (for example, a username and password previously registered), for example using wireless data over a mobile network or via a Wi-Fi hotspot, and the server returns profile data, or optionally profile data associated with a particular day, time, location, etc., as described previously, or optionally profile data specific to a requesting phone (e.g. a work phone versus a personal phone). Such an exchange may be performed whenever the phone pairs with an e-cigarette, and/or periodically. In principle, the e-cigarette could comprise this functionality directly, either using data or a Wi-Fi® hotspot.

Referring now to FIG. 7, a method of electronic aerosol/vapor provision for an electronic aerosol/vapor provision system, comprises:

In s710, measuring an airflow parameter within the electronic aerosol/vapor provision system (for example using the means described previously herein).

In s720, recalling one or more inhalation airflow profiles (for example using the means described previously herein).

In s730, comparing a measured airflow parameter with at least a first inhalation airflow profile while providing aerosol/vapor to a user (for example using the means described previously herein).

In s740, providing feedback to the user responsive to the difference between a compared measured airflow parameter and inhalation airflow profile (again for example using the means described previously herein). The feedback is provided in order to help the user adjust their inhalation action to generate an airflow within the e-cigarette that is closer to that of the profile, for example to help habituate the user to a desired vaping action (for example to reduce intake during working hours, or when driving).

It will be apparent to a person skilled in the art that variations in the above method corresponding to operation of the various embodiments of the apparatus as described and claimed herein are considered within the scope of the present disclosure, including but not limited to:

for a plurality of recalled inhalation airflow profiles, one profile being selected as the basis for feedback in dependence upon one or more selected from the list consisting of: time of day; day of week; location; type of aerosol/vapor being provided; and similarity to the measured airflow parameter, the feedback comprising a haptic feedback in which a haptic output is responsive (e.g. as per the examples of FIG. 8) to the difference between the compared measured airflow parameter and inhalation airflow profile, the feedback comprising a haptic feedback in which a one of a plurality of predetermined haptic outputs is selected in response to the difference between the compared measured airflow parameter and inhalation airflow profile, the feedback comprising an audio feedback in which an audio output is responsive to the difference between the compared measured airflow parameter and inhalation airflow profile, the feedback comprising an audio feedback in which a one of a plurality of predetermined audio outputs is selected in response to the difference between the compared measured airflow parameter and inhalation airflow profile, the feedback comprising a visual feedback in which an visual output is responsive to the difference between the compared measured airflow parameter and inhalation airflow profile, the feedback comprising a visual feedback in which a one of a plurality of predetermined visual outputs is selected in response to the difference between the compared measured airflow parameter and inhalation airflow profile, the feedback comprising a visual feedback in which a graphical representation of the difference between the compared measured airflow parameter and inhalation airflow profile is output, and the feedback being responsive to a real-time comparison between the compared measured airflow parameter and inhalation airflow profile.

It will be appreciated that the above methods may be carried out on conventional hardware suitably adapted as applicable by software instruction or by the inclusion or substitution of dedicated hardware, such as for example e-cigarette or similar, or an e-cigarette operating in combination with a mobile phone or similar.

Thus the required adaptation to existing parts of a conventional equivalent device may be implemented in the form of a computer program product comprising processor implementable instructions stored on a non-transitory machine-readable medium such as a floppy disk, optical disk, hard disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc, other than those specifically described herein. In addition, this disclosure may include other inventions not presently claimed, but which may be claimed in future.

The invention claimed is:

1. An electronic aerosol provision system comprising:
an airflow sensor operable to measure an airflow parameter;
a profile recall unit operable to recall one or more inhalation airflow profiles, describing at least one of a velocity or an amount of air inhaled through the electronic aerosol provision system over a course of a puff by a user; and
a comparison processing unit operable to compare a measured airflow parameter with at least a first inhalation airflow profile while providing aerosol to the user.

2. The electronic aerosol provision system according to claim 1, further comprising:

a feedback unit operable to provide feedback to the user responsive to a difference between the compared measured airflow parameter and the at least first inhalation airflow profile.

3. The electronic aerosol provision system according to claim 1, further comprising:
a mobile phone; and
an e-cigarette operable to communicate with the mobile phone, wherein the e-cigarette comprises the airflow sensor.

4. The electronic aerosol provision system according to claim 3, wherein the e-cigarette is operable to record the measured airflow parameter even when the e-cigarette is not in communication with the mobile phone, and is configured in these instances to subsequently transfer data pertaining to the measured airflow parameter when the e-cigarette is in communication with the mobile phone.

5. The electronic aerosol provision system according to claim 3, wherein the mobile phone comprises a user interface for recalling or setting the at least first inhalation airflow profile.

6. The electronic aerosol provision system according to claim 3, further comprising:
a feedback unit operable to provide feedback to the user responsive to a difference between the compared measured airflow parameter and the at least first inhalation airflow profile,
wherein the mobile phone comprises the feedback unit.

7. The electronic aerosol provision system according to claim 1, further comprising a display for providing a graphical representation of an inhalation airflow profile.

8. The electronic aerosol provision system according to claim 7, further comprising:
a mobile phone, wherein the mobile phone comprises the display; and
an e-cigarette operable to communicate with the mobile phone, wherein the e-cigarette comprises the airflow sensor.

9. The electronic aerosol provision system according to claim 7, wherein the display is further configured for providing a graphical representation of an inhalation of a user as a function of time.

10. The electronic aerosol provision system according to claim 1, wherein the profile recall unit comprises a communication unit operable to obtain from a remote server the one or more inhalation airflow profiles associated with an account of the user.

11. A non-therapeutic method of operating an electronic aerosol provision system, comprising:
measuring an airflow parameter within the electronic aerosol provision system;
recalling one or more inhalation airflow profiles describing at least one of a velocity or an amount of air inhaled through the electronic aerosol provision system over a course of a puff by a user; and
comparing a measured airflow parameter with at least a first inhalation airflow profile while providing aerosol to the user.

* * * * *